United States Patent [19]

Rowlands

[11] 4,166,858

[45] Sep. 4, 1979

[54] METHOD AND COMPOSITION FOR TREATING FLUKE INFECTIONS

[75] Inventor: Dewi T. Rowlands, Berkhamsted, England

[73] Assignee: Burroughs Wellcome Co., N.C.

[21] Appl. No.: 824,175

[22] Filed: Aug. 12, 1977

[30] Foreign Application Priority Data

Aug. 13, 1976 [GB] United Kingdom ............... 33827/76
Sep. 30, 1976 [GB] United Kingdom ............... 40722/76
Oct. 29, 1976 [GB] United Kingdom ............... 45027/76
Dec. 14, 1976 [GB] United Kingdom ............... 54053/76

[51] Int. Cl.$^2$ .................. A61K 31/415; A61K 31/165
[52] U.S. Cl. ................................ 424/273 B; 424/324
[58] Field of Search ............... 424/273 R, 273 B, 324

[56] References Cited

U.S. PATENT DOCUMENTS 3,929,821  12/1975  Beard et al. .......................... 424/273

OTHER PUBLICATIONS

Harfenist—Chem. Abst., vol. 77, (1972), p. 19404w.

*Primary Examiner*—Sam Rosen
*Attorney, Agent, or Firm*—Donald Brown

[57] ABSTRACT

A method of treating fluke infections in mammals comprising concurrent or sequential administration of an ether, such as diamphenethide having flukicidal properties and a potentiating benzimidazole, such as oxfendazole, and compositions therefor.

33 Claims, No Drawings

METHOD AND COMPOSITION FOR TREATING FLUKE INFECTIONS

This invention relates to the treatment and prophylaxis of helminth infections and formulations for this purpose. In particular it provides a combination of active ingredients which has been found particularly efficacious against liver fluke and other helminth infections.

Animals are infected with liver fluke when eating forage contaminated with encysted forms of cercariae, an intermediate stage in the life-cycle of the fluke. The cercariae emerge from the cysts in the intestine of the host animal, penetrate the intestine wall, and make their way to the liver. At this stage they are microscopic in size, but grow as they wander around the liver parenchyma. This causes considerable destruction of the liver tissue and can give rise to the syndrome of acute fascioliasis which normally leads to death of the host when massive infections are present. If the animal survives, the flukes eventually reach the bile ducts where they mature into the adult worms. The presence of a massive infection in the bile ducts gives rise to the syndrome of chronic fascioliasis which is a serious debilitating disease of the host animal.

It is already known from United Kingdom Patent Specification No. 1,380,882 that compounds of formula (A),

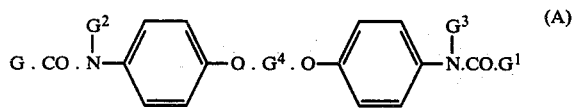

wherein G and $G^1$ are the same or different and each is hydrogen, an optionally substituted straight or branched saturated aliphatic hydrocarbon group having 1 to 7 carbon atoms, or an unsaturated aliphatic hydrocarbon group having 2 to 4 carbon atoms; $G^2$ and $G^3$ are the same or different and each is hydrogen or an alkyl group having 1 to 4 carbon atoms; $G^4$ is —CH$_2$—, —(CH$_2$)$_2$—, —CH$_2$—O—CH$_2$—, or the group

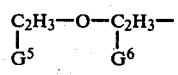

wherein $G^5$ and $G^6$ are the same or different and each is hydrogen or an alkyl group having 1 to 3 carbon atoms; and when $G^1$ or $G^2$ is a saturated aliphatic hydrocarbon group it may be substituted by a hydroxy group, an amino group, an N-alkylamino group, an N,N-dialkylamino group, or an acyl group for example an acetyl group, the 'alkyl' and 'acyl' groups referred to above each having from 1 to 4 carbon atoms, and acid addition salts thereof when either or both of G and $G^1$ includes an amino, N-alkylamino or N,N-dialkylamino group, have activity against infections of liver flukes in mammals. A preferred compoun of formula (I) is bis-($\beta$-(4-acetamidophenoxy)ethyl)ether (hereinafter referred to an diamphenethide) which is particularly effective in controlling infections of immature flukes. In order to provide adequate oral control of infections of all ages an oral dose of 120 mg/kg bodyweight of diamphenethide is required.

Whilst it is suggested in U.K. Patent Specification No. 1,380,882 that a compound such as diamphenethide might be conveniently administered in conjunction with a benzimidazole anthelmintic such as Thiabendazole, Parbendazole or Cambendazole in order to supplement or complement its activity, none of these compounds have been found to improve the efficacy of diamphenethide and in fact Thiabendazole at a dose of 50 mg/kg bodyweight was found to adversely affect the flukicidal activity of an identical dose of diamphenethide.

It has now been found that the minimum effective flukicidal dose of a compound of formula (A) may be considerably reduced upon concurrent or sequential administration of certain benzimidazoles hereinafter referred to as a "potentiating benzimidazole".

By a "potentiating benzimidazole" is meant one which, when administered in a specific amount concurrently or sequentially with diamphenethide, will decrease the minimum effective dose of the latter, and where the same amount administered alone provides inadequate control of a fluke infection. In particular a benzimidazole which when administered alone effects less than 70% clearance of a 12 week old F. hepatica infection in sheep but which at the same dose will decrease the minimum effective dose of diamphenethide to less than 120 mg/kg, preferably less than 90 mg/kg bodyweight.

By virtue of a "potentiating benzimidazole" being able to enhance or synergise the flukicidal activity of a compound of formula (A) the present invention provides for the combination of a compound of formula (A) or a salt thereof with a "potentiating benzimidazole" having a more efficacious flukicidal activity than might be expected from the separate activity of the components, except for the combination of diamphenethide with oxfendazole or a salt thereof.

Examples of potentiating benzimidazoles have been described in various publications including the following patent specifications.

In U.S. Pat. No. 3,929,821 there are described compounds of formula (B)

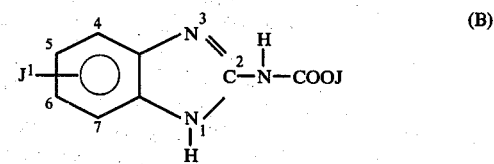

wherein J is lower alkyl group having 1 to 4 carbon atoms; $J^1$ is —SOJ$^2$, —SO$_2$J$^2$, —SCN, —SJ$^3$, OJ$^4$ or $J^5$(CH$_2$)$_n$J$^6$J$^7$ where $J^5$ and $J^6$ are independently

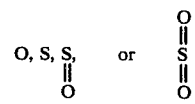

$J^7$ is lower alkyl, having 1 to 4 carbon atoms or aryl, and n is 1–4; $J^2$ is lower alkyl, cycloalkyl, lower alkenyl, lower alkynyl aralkyl or aryl; and $J^3$ is lower alkenyl, lower alkynyl or aralkyl; the $J^1$ substitution is at the 5(6)-position; the hydrogen on the nitrogen at the 1-position can be replaced with substituents which do not adversely affect the anthelmintic properties of the basic compound, including N-alkylcarbamoyl, N,N-dialkylcarbamoyl, N-alkoxycarbonylcarbamoyl, cyano, trichloromethylthio, alkylthio, phenylthio, nitrophenylthio, alkylsulfinyl, phenylsulfinyl, acyl, alkoxycarbonyl, benzoyl, alkoxycarbonylalkyl, carboxyalkyl, hydroxy and conventional esters and ethers thereof, etc. In formula (B) lower alkyl groups have from 1 to 6 carbon atoms, lower alkenyl or alkynyl groups have 3 to 6 carbon atoms, and each of alkyl, alkenyl and alkynyl may be further substituted by one or more radicals selected from thiocyanate, alkoxy, aryl, aroyl, hydroxy, cycloalkyl, halo, cyano and nitro radicals. Alkoxy groups have from 1 to 6 carbon atoms and cycloalkyl groups have from 3 to 7 carbon atoms. Aryl, aralkyl and aroyl groups may be substituted by one or more alkyl, alkoxy, halo, nitro, cyano, thiocyanato, isothiocyanato, trifluoromethyl, alkylthio, alkylsulfinyl, alkylsulfonyl, alkanoyl or alkanoylamino where the acyl portion has 1 to 6 carbon atoms, $-SO_2NJ^8$, $J^9$ or $-N(J^8)SO_2J^9$ radicals where $J^8$ and $J^9$ are independently hydrogen or lower alkyl.

The compounds of formula (B) and their salts are ascribed nematocidal properties being effective when administered at a daily dose of from 5 to 100 mg/kg bodyweight. A particularly active compound is methyl 5(6)-phenylsulphinyl-2-benzimidazolecarbamate, hereinafter referred to as oxfendazole.

Similarly, Netherlands Patent Application No. 7,408,386 describes compounds of formula (C)

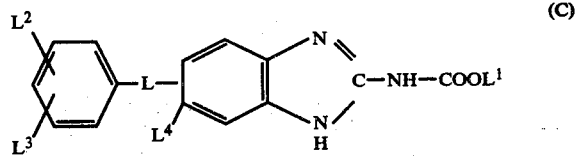

wherein $L^1$ is alkyl having 1 to 4 carbon atoms; $L^2$ and $L^3$ are independently hydrogen, hydroxy, alkoxy having 1 to 4 carbon atoms, halogen, trifluoromethyl, alkyl having 1 to 4 carbon atoms and carbalkoxy having 2 to 5 carbon atoms; $L^4$ is hydrogen or chloro and L is oxygen or sulphur.

The compounds of formula (C) and salts thereof are described as being active against a variety of nematode infections when administered at a dose of from 0.5 to 50 mg/kg bodyweight. A particularly active compound is methyl 5(6)-phenylthio-2-benzimidazolecarbamate, hereinafter referred to as fenbendazole.

In published South African Patent Specification No. 66/7255 there are described compounds of formula (D):

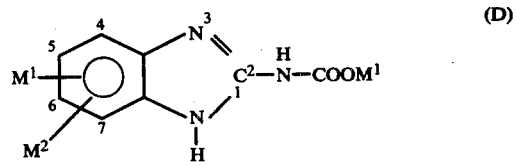

wherein $M^1$ is straight or branched alkyl having 1 to 6 carbon atoms, cycloalkyl having 3 to 10 carbon atoms, alkylcycloalkyl having 3 to 10 carbon atoms, straight or branched alkenyl or alkynyl each of 2 to 10 carbon atoms, or phenyl;

$M^1$ is hydrogen, straight or branched alkyl having 1 to 5 carbon atoms, phenyl, straight or branched alkoxy having 1 to 15 carbon atoms, hydroxyalkyl having 1 to 6 carbon atoms, trifluoromethyl, halo preferably chloro or bromo, hydroxy, alkylthio, alkylamino, dialkylamino, cyano, carboxy or carbalkoxy having 2 to 7 carbon atoms;

$M^2$ is hydrogen, alkyl or alkoxy each having 1 to 6 carbon atoms;

provided that $M^1$ and $M^2$ are not both hydrogen when $M^1$ is alkyl.

In formula (D), alkyl moieties have 1 to 7 carbon atoms unless otherwise specified.

The compounds of formula (D) are ascribed anthelmintic properties, being effective at a dose of from 2.5 to 10 mg/kg bodyweight.

A preferred compound of formula (D) is methyl 5(6)-n-propylthio-2-benzimidazole carbamate, hereinafter referred to as albendazole.

In U.S. Pat. No. 3,996,368 are described compounds of formula (E)

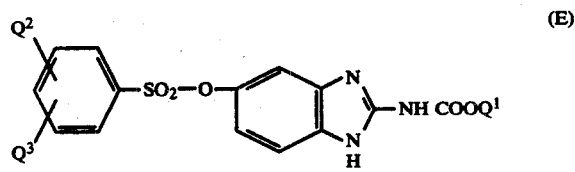

wherein $Q^1$ is alkyl having 1 to 4 carbon atoms, $Q^2$ and $Q^3$ are the same or different and each represents hydrogen, hydroxy, alkoxy having 1 to 4 carbon atoms, halo, trifluoromethyl, alkyl having 1 to 4 carbon atoms, alkoxycarbonyl having 1 to 4 carbon atoms in the alkoxy moiety or cyano.

In U.S. Pat. No. 3,996,369 are described compounds of formula (F)

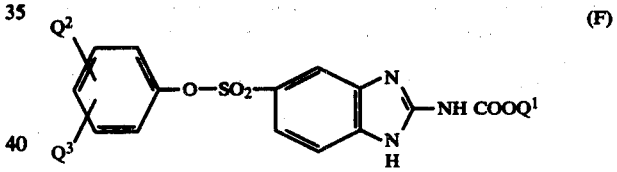

wherein $Q^1$, $Q^2$ and $Q^3$ each have the same meaning as in formula (E).

The compounds of formulae (E) and (F) are described as being active against helminths and liver flukes, the effective dose being in the range of from 0.5 to 50 mg/kg bodyweight. A particularly active compound is 3-trifluoromethylphenyl 2-methoxycarbonyl-5-benzimidazolesulphonate.

Compounds of formulae (B), (C), (D), (E) and (F) having a basic moiety are capable of forming acid addition salts, and those having an acidic moiety are capable of forming salts with cations.

Suitable acid addition salts of compounds of formulae (A) to (F) include those with inorganic acids such as, for example, sulphuric, sulphonic, sulphamic, nitric, phosphoric and hydrochloric acids and organic acids such as, for example, acetic, citric, lactic, palmitic, tartaric, succinic, maleic and benzoic acids. Suitable cations for forming salts with compounds of formulae (B) to (F) include for example an alkali metal cation such as sodium or potassium, an alkaline earth metal cation such as calcium or magnesium, ammonium or the cation of an organic base such as an amine, for example ethanolamine.

Preferred salts of the compounds of formula (A) to (F) are those which are pharmaceutically acceptable, by which is meant those which do not unduly diminsh the anthelmintic properties of the parent compound, and which are not injurious to the recipient thereof. As a further aspect of the present invention there is provided a combination of a compound of formula (A) as hereinabove defined or a salt thereof with a compound of formula (I)

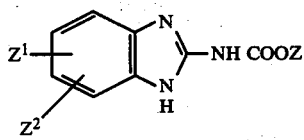

wherein
Z is alkyl having 1 to 4 carbon atoms;
$Z^1$ is a group —$SOZ^3$ or —$SO_2Z^3$ such that $Z^3$ is lower alkyl, lower alkenyl, lower alkynyl, cycloalkyl, aralkyl or aryl;
—$SZ^4$ such that $Z^4$ is lower alkenyl, lower alkynyl, aralkyl, alkyl having 1 to 7 carbon atoms or phenyl optionally substituted by one or two groups independently selected from hydroxy, alkyl of 1 to 4 carbon atoms, alkoxy of 1 to 4 carbon atoms, alkoxycarbonyl of 2 to 5 carbon atoms, halogen and trifluoromethyl;
—$OZ^5$ such that $Z^5$ is lower alkenyl, lower alkynyl, aralkyl, alkyl having 1 to 15 carbon atoms or phenyl optionally substituted by one or two groups independently selected from hydroxy, alkyl of 1 to 4 carbon atoms, alkoxy of 1 to 4 carbon atoms, alkoxycarbonyl of 2 to 5 carbon atoms, halogen and trifluoromethyl;
—$OSO_2Z^6$ or —$SO_2OZ^6$ such that $Z^6$ is phenyl optionally substituted by one or two groups independently selected from hydroxy, alkoxy of 1 to 4 carbon atoms, alkyl of 1 to 4 carbon atoms, alkoxycarbonyl of 1 to 4 carbon atoms in the alkyl moiety, halo, trifluoromethyl and cyano;
—$Z^7(CH_2)_nZ^8.Z^9$ wherein $Z^7$ and $Z^8$ are independantly selected from —O—, —S—, —SO— and —$SO_2$—, $Z^9$ is lower alkyl of 1 to 4 carbon atoms or aryl and n is 1 to 4; or $Z^1$ is alkyl having 1 to 6 carbon atoms, phenyl, hydroxyalkyl of 1 to 6 carbon atoms, trifluoromethyl, halogen, hydroxy, alkylamino or dialkylamino wherein the alkyl moieties each have 1 to 7 carbon atoms, carboxy, alkoxycarbonyl having 2 to 7 carbon atoms in the alkyl moiety, cyano or cyanothio; and $Z^2$ is hydrogen; or when $Z^1$ is alkyl of 1 to 5 carbon atoms, phenyl alkoxy, hydroxyalkyl, trifluoromethyl, halogen, hydroxy, alkylthio, alkylamino, dialkylamino, cyano, carboxy or alkoxycarbonyl then $Z^2$ may be alkyl or alkoxy each of 1 to 6 carbon atoms; or when $Z^1$ is optionally substituted phenoxy or phenylthio then $Z^2$ may be chloro in the 5- or 6-position; provided that when $Z^1$ has the same meaning as J in formula (B) then the 1-position of the benzimidazole nucleus may be substituted in the manner hereinbefore defined in formula (B); and when $Z^1$ is optionally substituted phenoxy or phenylthio then Z may have the same meaning as M in formula (D); or a salt thereof; but excluding the combination of diamphenethide with oxfendazole or a salt thereof.

Particularly active "potentiating benzimidazoles" are those having a 2-alkoxycarbonylamino group, in particular a 2-methoxycarbonylamino group, for example compounds of formula (I) wherein Z is alkyl such as methyl. A further structural feature found in certain "potentiating benzimidazoles" is a 5(6)-substituent preferably having an oxygen or sulphur atom adjacent the benzimidazole nucleus.

Especially preferred combinations included within the scope of the present invention are those comprising diamphenethide in association with at least one selected from fenbendazole, methyl 5(6)-(3-trifluoromethylphenyloxysulphonyl)-2-benzimidazole carbamate and albendazole; and those comprising a compound of formula (A) other than diamphenethide in association with at least one selected from oxfendazole, fenbendazole, albendazole and methyl 5(6)-(3-trifluoromethylphenoxysulphonyl)-2-benzimidazolecarbamate.

In addition to decreasing the total amount of drug given, a further advantage of combining a compound of formula (A) with a potentiating benzimidazole is that the combined product is effective against a broad spectrum of helminth infections. This is particularly convenient since in practice it is often found that fluke and other worm infections occur at approximately the same time, and the combined treatment requires only one dosing of each animal to control all of the infections.

In a combination of a compound of formula (A) with a "potentiating benzimidazole" for the control of fluke infections an appropriate amount of the compound of formula (A) will generally lie in the range of from 20 to 150, for example from 20 to 100 mg/kg bodyweight and the amount of potentiating benzimidazole from 2.5 to 50 mg/kg bodyweight, although the amount of compound of formula (A) may be increased if desired. However the optimum effective dose will of course vary with the particular compounds chosen, the nature of the host and the severity, nature and age of the infection; but it has been found that in sheep the preferred dose is from 40 to 60, for example about 50 mg/kg bodyweight of a compound of formula (A) in particular when diamphenethide is used, and from 5 to 10 mg/kg bodyweight of "potentiating benzimidazole" in particular when oxfendazole albendazole, methyl 5(6)-(3-trifluoromethylphenoxysulphonyl)-2-benzimidazole carbamate or fenbendazole is used. Similar doses for cattle are from 60 to 100, for example 95 mg/kg compound of formula (A) with from 3 to 6 mg/kg bodyweight, "potentiating benzimidazole".

The combination of a compound of formula (A) together with a "potentiating benzimidazole" or a salt thereof other than diamphenethide with oxfendazole or a salt thereof (hereinafter referred to as the "Combination") may be administered to mammals to control fluke and nematode infections; and if administered concurrently the Combination may take the form of a simple mixture of ingredients, separate formulations of each ingredient or a single formulation of both ingredients.

Such a Combination may be used for the treatment or prophylaxis of *F. hepatica* infections in ruminants including sheep, cattle, goat, buffalo and horse; and *F. gigantica* in mice and ruminants including sheep, buffalo and cattle. The Combination will also control gastrointestinal nematode infections which the host may also possess.

For the purpose of controlling helminth infections the Combination comprises the compound of formula (A) or a salt thereof and the "potentiating benzimidazole" in the proportion of from 1:1 to 50:1 and preferably from 5:1 to 30:1 for example about 10:1 and about 25:1.

Although the Combination may be administered as a mixture of the raw chemicals, it is preferably formulated together in the customary formulations which additionally contain one or more inert carriers materials commonly used in pharmaceutical compositions as a vehicle for active ingredients.

The compositions may take the form of discrete units such as boluses or pellets each containing a predetermined amount of the active ingredient.

For example unit dose compositions of the Combination may comprise upto 15 g. of the Combination but generally smaller units are used. For example boluses for adminstration to cattle conveniently contain from 2 to 12 and preferably about from 7 to 10 g. of the Combination, whereas boluses for administration to sheep contain up to 4, for example from 1 to 3 g. of the Combination. Such boluses in addition may comprise the usual excipients such as diluents, disintegrating agents, surface active agents and lubricants.

Alternatively the Combination may be presented as a solution or suspension in a water-in-oil liquid emulsion, for example as a liquid drench. Such compositions may additionally contain such other conventional agents as preservatives, thickening agents, wetting and dispersing agents, buffers, humectants, emulsifying agents, fillers, emoluents and surface active agents.

The Combination may further be presented as a powder or granules, an electuary or paste, in salt licks or block licks or in the feed or as a feed supplement intended for the host animal, for example as a premix.

The compositions may be made by any of the methods of pharmacy but all methods include the step of bringing into association by admixture the Combination with the carrier which constitutes one or more accessory ingredients. In general the compositions are prepared by uniformly and intimately bringing into association the active ingredient with liquid carriers or finely divided solid carriers or both, and then, if necessary, shaping the product into the desired composition. The compositions contain one or more of the usual accessory ingredients used to prepare anthelmintic compositions.

Any method known in the art may be used for the synthesis of the compounds of formula (A) and the "potentiating benzimidazoles" for example those described in the patent specifications identified hereinabove, the contents of which specifications are hereby incorporated by reference.

The present invention therefore comprises in summary the following aspects which we will claim, but the following aspects are not intended to be exhaustive:

(a) The combination of a compound of formula (A) or a salt thereof with a "potentiating benzimidazole", except for the combination of diamphenethide with oxfendazole.

(b) The combination of a compound of formula (A) with a compound of formula (B), (C), (D), (E) or (F) or a salt thereof except for the combination of diamphenethide with oxfendazole.

(c) A veterinary composition comprising an effective flukicidal or nematocidal amount of a combination defined in (a) or (b).

(d) A method of controlling fluke or helminth infections in a mammal comprising concurrent or sequential administration of a non-toxic effective flukicidal or nematocidal amount of a combination defined in (a) or (b).

The following examples are provided to illustrate the invention but are not intended to be construed as a limitation thereof.

In the following examples, provided to illustrate veterinary compositions of the present invention, the following substances are used:

Bevaloid dispersant: a naphthalene formaldehyde sulphonic acid condensate;
Keltrol F: xantham gum, polysaccharide B-1459;
Aerosol OT: dioctyl sodium sulfosuccinate;
Myrj 52 (Trade Name): Polysorbate 60, a polyoxyethylene derivative of fatty acid;
Ethylan KEO: an ethylene oxide nonylphenyl condensate;
Neosyl: a fine silica filler;
Natrosol 250: hydroxyethylcellulose.

In these examples "Ether" means a compound of formula (A) and "Benzimidazole" means a "Potentiating Benzimidazole" as hereinbefore defined except that when oxfendazole is used the Ether may not be diamphenethide but may for example be bis($\beta$-(4-formamidephenoxy)ethyl)ether, hereinafter referred to as "BFP". The compound methyl 5(6)-(3-trifluoromethylphenoxysulphonyl)-2-benzimidazolecarbamate is hereinafter referred to as "TBC".

EXAMPLE A

| LIQUID DRENCH | | SHEEP | CATTLE |
|---|---|---|---|
| (a) | Benzimidazole | 1.75 | 2.00 |
| | Ether | 15.00 | 20.00 |
| | Bevaloid | 1.00 | 1.00 |
| | Sodium Benzoate | 1.00 | 1.00 |
| | Thymol | 0.04 | 0.04 |
| | Bentonite | 3.00 | 3.00 |
| | Water | 78.21 | 72.96 |
| | | 100.00% | 100.00% |
| (b) | Oxfendazole | 1.50 | 0.8 |
| | BFP | 15.00 | 21.0 |
| | Sorbic Acid | 0.50 | 0.50 |
| | Citric Acid | 0.40 | 0.40 |
| | Sodium citrate | 0.90 | 0.90 |
| | Keltrol | 0.10 | 0.10 |
| | Aerosol OT | 0.15 | 0.15 |
| | Water | 81.45 | 76.15 |
| | | 100.00 | 100.00 |
| (c) | Fenbendazole | 1.75 | 2.00 |
| | Diamphenethide | 15.0 | 20.00 |
| | Myrj 52 | 2.5 | 2.5 |
| | Parachlorometacresol | 0.2 | 0.2 |
| | Sodium carboxymethyl cellulose | 0.8 | 0.8 |
| | Water | 79.75 | 74.5 |
| | | 100.00 | 100.00 |
| (d) | Albendazole | 1.05 | 0.80 |
| | Diamphenethide | 15.00 | 21.00 |
| | Bevaloid Dispersant | 1.00 | 1.00 |
| | Sodium Benzoate | 1.00 | 2.00 |
| | Thymol | 0.04 | 0.04 |
| | Bentonite | 3.00 | 3.00 |
| | Water | 78.91 | 73.16 |
| | | 100.00 | 100.00 |
| (e) | TBC | 1.50 | 0.8 |
| | Diamphenethide | 15.00 | 21.0 |
| | Sorbic Acid | 0.50 | 0.50 |
| | Citric Acid | 0.40 | 0.40 |
| | Sodium citrate | 0.90 | 0.90 |
| | Keltrol F | 0.10 | 0.10 |
| | Aerosol OT | 0.15 | 0.15 |
| | Water | 81.45 | 76.15 |
| | | 100.00% | 100.00% |

EXAMPLE B

PASTE

| (a) | Ether | 58.00 | 60.00 |
|---|---|---|---|
| | Benzimidazole | 7.25 | 6.00 |
| | Glycerin | 3.30 | 3.20 |
| | Ethylan KEO | 2.00 | 2.00 |
| | Natrosol 250 | 0.20 | 0.20 |
| | Nipagin M | 0.10 | 0.10 |
| | Sorbitan monooleate | 0.40 | 0.40 |
| | Cetostearyl alcohol | 3.25 | 3.40 |
| | Mineral oil | 13.00 | 12.80 |
| | Water | 11.00 | 11.90 |
| | | 100.00 | 100.00 |

| | | SHEEP | CATTLE |
|---|---|---|---|
| (b) | BFP | 50.00 | 52.50 |
| | Oxfendazole | 5.00 | 2.00 |
| | Bevaloid dispersant | 0.40 | 0.40 |
| | Glycerin | 8.60 | 8.60 |
| | Gum Tragacanth | 1.80 | 1.80 |
| | Thymol | 0.04 | 0.04 |
| | Water | 34.16 | 34.66 |
| | | 100.00% | 100.00% |
| (c) | Diamphenethide | 24.00 | 25.00 |
| | Fenbendazole | 3.00 | 2.5 |
| | Bevaloid dispersant | 1.00 | 1.00 |
| | Glycerin | 23.00 | 23.00 |
| | Parachlorometacresol | 0.20 | 0.20 |
| | Neosyl | 15.00 | 15.00 |
| | Keltrol | 0.50 | 0.50 |
| | Water | 32.30 | 32.80 |
| | | 100.00% | 100.00% |
| (d) | Diamphenethide | 20.00 | 10.00 |
| | TBC | 2.50 | 1.00 |
| | Petroleum Jelly | 10.00 | 20.00 |
| | Mineral Oil | 50.00 | 40.00 |
| | Kaolin BP | 17.50 | 29.00 |
| | | 100.00% | 100.00% |
| (e) | Albendazole | 4.20 | 1.00 |
| | Diamphenethide | 60.00 | 26.20 |
| | Glycerin | 3.50 | 3.30 |
| | Ethylan KEO | 2.00 | 2.00 |
| | Natrosol 250 | 0.20 | 0.20 |
| | Nipagin M | 0.10 | 0.10 |
| | Sorbitan monooleate | 0.40 | 0.40 |
| | Ceto stearyl alcohol | 3.50 | 3.50 |
| | Mineral Oil | 13.50 | 13.00 |
| | Water | 12.60 | 12.10 |
| | | 100.00% | 100.00% |

EXAMPLE C

| PREMIX | | SHEEP | | CATTLE | |
|---|---|---|---|---|---|
| (a) | Benzimidazole | 1 w/w | 8 w/w | 8.0 w/w | 1.0 w/w |
| | Ether | 8 | 64 | 80.0 | 10.0 |
| | Maize Meal | 91 | 28 | 12.0 | 89.0 |
| | | 100% | 100% | 100.0% | 100.0% |
| (b) | Benzimidazole | 1 | 8 | 28.0 | 1.0 |
| | Ether | 8 | 64 | 80.0 | 10.0 |
| | Calcium carbonate | 91 | 28 | 12.0 | 89.0 |
| | | 100% | 100% | 100.0% | 100.0% |

EXAMPLE 1

Treatment of *F. Hepatica* Infection in Sheep

Cheviot and Dorset Down sheep, approximately fifteen months old, were experimentally infected with *F. hepatica* by giving each animal about 200 metacercariae in water by drenching bottle. Twelve weeks after commencement of the infection each sheep, other than controls, was treated with diamphenethide, a benzimidazole or a combination of the two, and two weeks after treatment the sheep were slaughtered and examined for the presence of fluke. Details of the treatment and its efficacy (expressed as percentage reduction in the number of flukes which were found as compared with untreated controls) are given in Table 1.

TABLE 1

| No. of Sheep | Treatment | % Clearance |
|---|---|---|
| 6 | Control | 0 |
| 6 | 50 mg/kg diamphenethide | 13 |
| 6 | 5 mg/kg fenbendazole | 8 |
| 6 | 50 mg/kg diamphenethide + 5 mg/kg fenbendazole | 32 |
| 5 | 4 mg/kg albendazole | 64 |
| 5 | 50 mg/kg diamphenethide + 4 mg/kg albendazole | 80 |

What we claim is:

1. A combination suitable for use in treating fluke infections in mammals comprising an effective anthelmintic amount of a compound of formula (A):

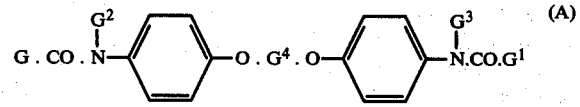

wherein G and $G^1$ are the same or different and each is hydrogen, a substituted or unsubstituted straight or branched saturated aliphatic hydrocarbon group having 1 to 7 carbon atoms, or an unsaturated aliphatic hydrocarbon group having 2 to 4 carbon atoms; $G^2$ and $G^3$ are the same or different and each is hydrogen or an alkyl group having 1 to 4 carbon atoms; $G^4$ is —CH$_2$—, —(CH$_2$)$_2$—, —CH$_2$—O—CH$_2$—, or the group

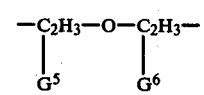

wherein $G^5$ and $G^6$ are the same or different and each is hydrogen or an alkyl group having 1 to 3 carbon atoms; and when $G^1$ or $G^2$ is a saturated aliphatic hydrocarbon group it may be substituted by a hydroxy group, an amino group, an N-alkylamino group, an N,N-dialkylamino group, or an alkanoyl group, wherein 'alkyl' and 'alkanoyl' groups each have from 1 to 4 carbon atoms, or a salt thereof taken together with an effective flukicidal potentiating amount of a potentiating benzimidazole, being a benzimidazole which when administered alone at a specific dose effects less than 70% clearance of a 12 week old *F. hepatica* infection in sheep but which at the same dose will decrease the minimum flukicidal effective dose of diamphenethide to less than 120 mg/kg, provided that when the compound of formula (A) is diamphenethide the potentiating benzimidazole is other than oxfendazole or a salt thereof.

2. The combination of claim 1 wherein the benzimidazole has a 2-alkoxycarbonylamino substituent.

3. The combination of claim 1 wherein the benzimidazole has a 5(6)-substituent.

4. The combination of claim 1 wherein the benzimidazole is selected from methyl 5(6)-phenylsulphinyl-2-benzimidazole carbamate;
methyl 5(6)-phenylthio-2-benzimidazole carbamate;
methyl 5(6)-n-propylthio-2-benzimidazole carbamate;
methyl 5(6)-(3-trifluoromethylphenoxysulphonyl)-1-benzimidazole carbamate and salts thereof.

5. The combination of claim 1 wherein the compound of formula (A) is diamphenethide and the benzimidazole is other than oxfendazole or a salt thereof.

6. A combination as claimed in claim 1 wherein the ratio of the compound of formula (A) to potentiating benzimidazole is in the range of from 1:1 to 50:1.

7. A combination as claimed in claim 6 wherein the ratio is from 5:1 to 30:1.

8. A composition suitable for use in the treatment of liver fluke infection in a mammal comprising a combination as claimed in claim 1 in association with an inert carrier.

9. A composition as claimed in claim 8 suitable for oral administration.

10. A composition as claimed in claim 8 comprising from 5 to 95% by weight of the combination.

11. A composition as claimed in claim 8 wherein the carrier includes a solid diluent.

12. A composition as claimed in claim 8 wherein the carrier includes a liquid diluent.

13. A composition as claimed in claim 8 in the form of a bolus.

14. A composition as claimed in claim 8 in the form of a paste.

15. A composition as claimed in claim 8 in the form of a liquid drench.

16. A composition as claimed in claim 8 when incorporated into animal feedstuff or a premix therefor.

17. A composition as claimed in claim 8 in the form of a unit dose comprising up to 15 grammes of the combination.

18. A combination for use in treating fluke infections in mammals comprising a compound of formula (A):

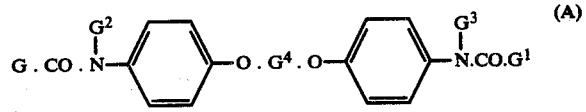

wherein G and $G^1$ are the same or different and each is hydrogen, a substituted or unsubstituted straight or branched saturated aliphatic hydrocarbon group having 1 to 7 carbon atoms, or an unsaturated aliphatic hydrocarbon group having 2 to 4 carbon atoms; $G^2$ and $G^3$ are the same or different and each is hydrogen or an alkyl group having 1 to 4 carbon atoms; $G^4$ is $-CH_2-$, $-(CH_2)_2-$, $-CH_2-O-CH_2-$, or the group

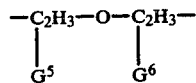

wherein $G^5$ and $G^6$ are the same or different and each is hydrogen or an alkyl group having 1 to 3 carbon atoms; and when $G^1$ or $G^2$ is a saturated aliphatic hydrocarbon group it may be substituted by a hydroxy group, an amino group, an N-alkylamino group, an N,N-dialkylamino group, or an alkanoyl group, wherein 'alkyl' and 'alkanoyl' groups each have from 1 to 4 carbon atoms, or a salt thereof taken together with an effective flukicidal potentiating amount of a benzimidazole of formula (I):

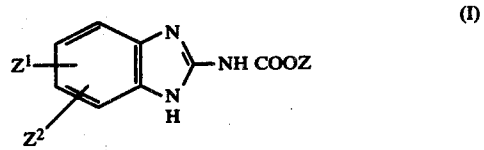

wherein
Z is alkyl having 1 to 4 carbon atoms;
$Z^1$ is a group $-SOZ^3$ or $-SO_2Z^3$ such that $Z^3$ is lower alkyl, lower alkenyl, lower alkynyl, cycloalkyl, aralkyl or aryl;
$-SZ^4$ such that $Z^4$ is lower alkenyl, lower alkynyl, aralkyl, alkyl having 1 to 7 carbon atoms or phenyl which is unsubstituted or substituted by one or two groups independently selected from hydroxy, alkyl of 1 to 4 carbon atoms, alkoxy of 1 to 4 carbon atoms, alkoxycarbonyl of 2 to 5 carbon atoms, halogen and trifluoromethyl;
$-OZ^5$ such that $Z^5$ is lower alkenyl, lower alkynyl, aralkyl, alkyl having 1 to 15 carbon atoms or phenyl which is unsubstituted or substituted by one or two groups independently selected from hydroxy, alkyl of 1 to 4 carbon atoms, alkoxy of 1 to 4 carbon atoms, alkoxycarbonyl of 2 to 5 carbon atoms, halogen and trifluoromethyl;
$-OSO_2Z^6$ or $-SO_2OZ^6$ such that $Z^6$ is phenyl which is unsubstituted or substituted by one or two groups independently selected from hydroxy, alkoxy of 1 to 4 carbon atoms, alkyl of 1 to 4 carbon atoms, alkoxycarbonyl of 1 to 4 carbon atoms in the alkyl moiety, halo, trifluoromethyl and cyano;
$-Z^7(CH_2)_nZ^8.Z^9$ wherein $Z^7$ and $Z^8$ are independently selected from $-O-$, $-S-$, $-SO-$ and $-SO_2-$, $Z^9$ is lower alkyl of 1 to 4 carbon atoms and aryl and n is 1 to 4; or $Z^1$ is alkyl having 1 to 6 carbon atoms, phenyl, hydroxyalkyl of 1 to 6 carbon atoms, trifluoromethyl, halogen, hydroxy, alkylamino or dialkylamino wherein the alkyl moieties each have 1 to 7 carbon atoms, carboxy, alkoxycarbonyl having 2 to 7 carbon atoms in the alkyl moiety, cyano or cyanothio; and
$Z^2$ is hydrogen; or when $Z^1$ is alkyl of 1 to 5 carbon atoms, phenyl, alkoxy, hydroxyalkyl, trifluoromethyl, halogen, hydroxy, alkylthio, alkylamino, dialkylamino, cyano, carboxy or alkoxycarbonyl then $Z^2$ may be alkyl or alkoxy each of 1 to 6 carbon atoms; or when $Z^1$ is optionally substituted phenoxy or phenylthio then $Z^2$ may be chloro in the 5- or 6-position;
provided that when $Z^1$ is substituted or unsubstituted phenoxy or substituted or unsubstituted phenylthio then Z may be straight or branched alkyl having 1 to 6 carbon atoms, cycloalkyl having 3 to 10 carbon atoms, alkylcycloalkyl having 3 to 10 carbon atoms, straight or branched alkenyl or alkynyl each of 2 to 10 carbon atoms, or phenyl;
or a salt thereof, provided that when the compound of formula (A) is diamphenethide then the compound of formula (I) is other than oxfendazole or a salt thereof.

19. The combination of claim 18 wherein the compound of formula (I) is a benzimidazole of formula (B):

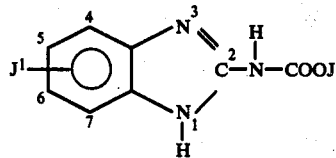

(B)

wherein J is lower alkyl group having 1 to 4 carbon atoms; $J^1$ is $-SOJ^2$, $-SO_2J^2$, $-SCN$, $-SJ^3$, $OJ^4$ or $J^5(CH_2)_nJ^6J^7$ where $J^5$ and $J^6$ are independently

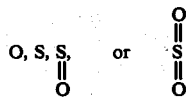

$J^7$ is lower alkyl, having 1 to 4 carbon atoms or aryl, and n is 1 to 4; $J^2$ is lower alkyl, cycloalkyl, lower alkenyl, lower alkynyl, aralkyl or aryl; and $J^3$ is lower alkenyl, lower alkynyl or aralkyl; and the $J^1$ substitution is at the 5(6)- position or a salt thereof.

20. The combination of claim 18 wherein the compound of formula (I) is a benzimidazole of formula (C):

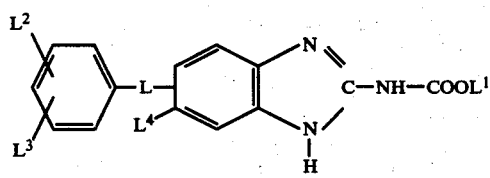

wherein $L^1$ is alkyl having 1 to 4 carbon atoms; $L^2$ and $L^3$ are independently hydrogen, hydroxy, alkoxy having 1 to 4 carbon atoms, halogen, trifluoromethyl, alkyl having 1 to 4 carbon atoms and carbalkoxy having 2 to 5 carbon atoms; $L^4$ is hydrogen or chloro and L is oxygen or sulphur, or a salt thereof.

21. The combination of claim 18 wherein the compound of formula (I) is a benzimidazole of formula (D):

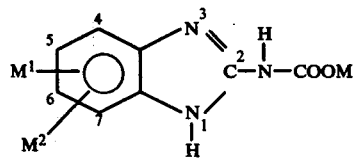

wherein

M is straight or branched alkyl having 1 to 6 carbon atoms, cycloalkyl having 3 to 10 carbon atoms, alkylcycloalkyl having 3 to 10 carbon atoms, straight or branched alkenyl or alkynyl each of 2 to 10 carbon atoms, or phenyl;

$M^1$ is hydrogen, straight or branched alkyl having 1 to 5 carbon atoms, phenyl, straight or branched alkoxy having 1 to 15 carbon atoms, hydroxyalkyl having 1 to 6 carbon atoms, trifluoromethyl, halo preferably chloro or bromo, hydroxy, alkylthio, alkylamino, dialkylamino, cyano, carboxy or carbalkoxy having 2 to 7 carbon atoms;

$M^2$ is hydrogen, alkyl or alkoxy each having 1 to 6 carbon atoms;

provided that $M^1$ and $M^2$ are not both hydrogen when M is alkyl, or a salt thereof.

22. The combination of claim 18 wherein the compound of formula (I) is a benzimidazole of formula (E):

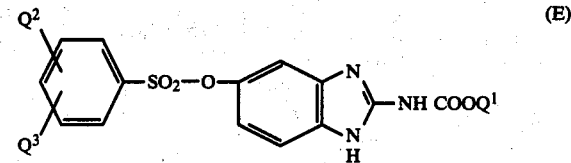

wherein $Q^1$ is alkyl having 1 to 4 carbon atoms, $Q^2$ and $Q^3$ are the same or different and each represents hydrogen, hydroxy, alkoxy having 1 to 4 carbon atoms, halo, trifluoromethyl, alkyl having 1 to 4 carbon atoms, alkoxycarbonyl having 1 to 4 carbon atoms in the alkoxy moiety or cyano, or a salt thereof.

23. The combination of claim 18 wherein the compound of formula (I) is a benzimidazole of formula (F):

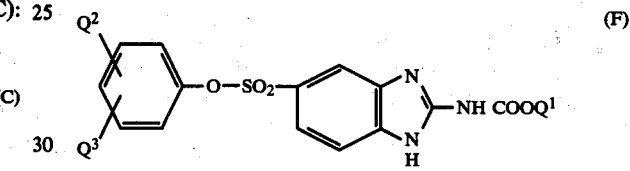

wherein $Q^1$ is alkyl having 1 to 4 carbon atoms, $Q^2$ and $Q^3$ are the same or different and each represents hydrogen, hydroxy, alkoxy having 1 to 4 carbon atoms, halo, trifluoromethyl, alkyl having 1 to 4 carbon atoms, alkoxycarbonyl having 1 to 4 carbon atoms in the alkoxy moiety or cyano or a salt thereof.

24. A method of treating a fluke infection in a mammal comprising the administration to said mammal of an effective flukicidal amount of a compound of formula (A)

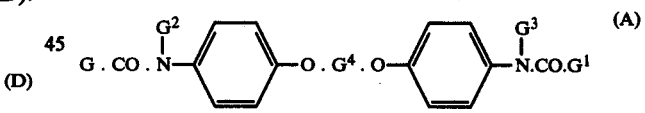

where G and $G^1$ are the same or different and each is hydrogen, a substituted or unsubstituted straight or branched saturated aliphatic hydrocarbon group having 1 to 7 carbon atoms, or an unsaturated aliphatic hydrocarbon group having 2 to 4 carbon atoms; $G^2$ and $G^3$ are the same or different and each is hydrogen or an alkyl group having 1 to 4 carbon atoms; $G^4$ is $-CH_2-$, $-(CH_2)_2-$, $-CH_2-O-CH_2-$, or the group

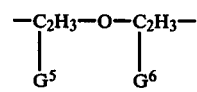

wherein $G^5$ and $G^6$ are the same or different and each is hydrogen or an alkyl group having 1 to 3 carbon atoms; and when $G^1$ or $G^2$ is a saturated aliphatic hydrocarbon group it may be substituted by a hydroxy group, an amino group, an N-alkylamino group, an N,N-dialkylamino group, or an alkanoyl group, wherein 'alkyl' and 'alkanoyl' groups each have from 1 to 4 carbon atoms, or a salt thereof, and a potentiating benzimidazole which when administered alone at a specific dose effects less than 70% clearance of a 12 week old *F. hepatica* infection in sheep but which at the same dose will decrease the minimum flukicidal effective dose of diamphenethide to less than 120 mg/kg, presented concurrently provided that when the compound of formula (A) is diamphenethide then the benzimidazole is other than oxfendazole or a salt thereof.

25. A method as claimed in claim 24 wherein the compound of formula (A) is diamphenethide.

26. A method as claimed in claim 24 for treating a fluke infection in sheep which comprises administration of from 40 to 60 mg/kg bodyweight of a compound of formula (A) with from 2.5 to 10 mg/kg bodyweight of benzimidazole.

27. A method as claimed in claim 24 for treating a fluke infection in cattle which comprises administration in the range of from 60 to 100 mg/kg bodyweight of a compound of formula (A) with from 3 to 6 mg/kg of benzimidazole.

28. A method as claimed in claim 24 wherein the compound of formula (A) and benzimidazole are administered orally.

29. A method of treating a fluke infection in a mammal comprising the administration to said mammal of an effective flukicidal amount of a compound of formula (A)

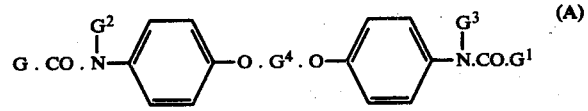
(A)

wherein G and $G^1$ are the same or different and each is hydrogen, a substituted or unsubstituted straight or branched saturated aliphatic hydrocarbon group having 1 to 7 carbon atoms, or an unsaturated aliphatic hydrocarbon group having 2 to 4 carbon atoms; $G^2$ and $G^3$ are the same or different and each is hydrogen or an alkyl group having 1 to 4 carbon atoms; $G^4$ is $-CH_2-$, $-(CH_2)_2-$, $-CH_2-O-CH_2-$, or the group

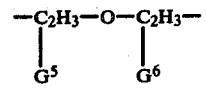

wherein $G^5$ and $G^6$ are the same or different and each is hydrogen or an alkyl group having 1 to 3 carbon atoms; and when $G^1$ or $G^2$ is a saturated aliphatic hydrocarbon group it may be substituted by a hydroxy group, an amino group, an N-alkylamino group, an N,N-dialkylamino group, or an alkanoyl group, wherein 'alkyl' and 'alkanoyl' groups each have from 1 to 4 carbon atoms, or a salt thereof and a potentiating benzimidazole which when administered alone at a specific dose effects less than 70% clearance of a 12 week old *F. hepatica* infection in sheep but which at the same dose will decrease the minimum flukicidal effective dose of diamphenethide to less than 120 mg/kg, presented sequentially, provided that when the compound of formula (A) is diamphenethide than the benzimidazole is other than oxfendazole or a salt thereof.

30. A method as claimed in claim 29 in which the compound of formula A is diamphenethide.

31. A method as claimed in claim 29 for treating a fluke infection in sheep which comprises administration of from 40 to 60 mg/kg bodyweight of a compound of formula (A) with from 2.5 to 10 mg/kg bodyweight of benzimidazole.

32. A method as claimed in claim 29 for treating a fluke infection in cattle which comprises administration in the range of from 60 to 100 mg/kg bodyweight of a compound of formula A with from 3 to 6 mg/kg of benzimidazole.

33. A method as claimed in claim 29 wherein the compound of formula A and benzimidazole are administered orally.

* * * * *